(12) United States Patent
Coleman

(10) Patent No.: US 7,090,833 B2
(45) Date of Patent: Aug. 15, 2006

(54) HOMEOPATHIC GENTLE SHAMPOO-CONDITIONER HEAD LICE REPELLENT AND NIT REMOVAL AID

(76) Inventor: George Coleman, P.O. Box 91, Jamesville, VA (US) 23398

( * ) Notice: Subject to any disclaimer, the term of this patent is extended or adjusted under 35 U.S.C. 154(b) by 112 days.

(21) Appl. No.: 10/433,378

(22) PCT Filed: Jan. 23, 2002

(86) PCT No.: PCT/US02/01786

§ 371 (c)(1),
(2), (4) Date: May 30, 2003

(87) PCT Pub. No.: WO02/060398

PCT Pub. Date: Aug. 8, 2002

(65) Prior Publication Data

US 2004/0037798 A1    Feb. 26, 2004

Related U.S. Application Data

(60) Provisional application No. 60/264,843, filed on Jan. 29, 2001.

(51) Int. Cl.
*A61K 8/00* (2006.01)
*A61Q 5/00* (2006.01)
*C11D 1/62* (2006.01)

(52) U.S. Cl. ............... 424/70.1; 424/70.19; 424/70.28

(58) Field of Classification Search ................ 424/70.1
See application file for complete search history.

(56) References Cited

U.S. PATENT DOCUMENTS 4,518,593 A * 5/1985 Juvin et al. .................. 424/745
5,578,298 A    11/1996 Berthiaume et al.
5,641,480 A *  6/1997 Vermeer .................. 424/70.24

FOREIGN PATENT DOCUMENTS

GB     2 343 625 A    5/2000
GB     2343625    *    5/2000

OTHER PUBLICATIONS http://www.headlice.org/news/2005/growingmenace.htm.*
http://www.homeoconsult.com/cntnt/about-homeopathy.shtml—2 pages.

* cited by examiner

Primary Examiner—Carlos A. Azpuru
Assistant Examiner—David Vanik
(74) Attorney, Agent, or Firm—Edward J. Kaliski

(57) ABSTRACT

A shampoo/conditioner that repels lice and aids in the removal of head lice and nits is presented. It is a formulation comprising at least one homeopathic louse insecticide included with acetic acid in association with a gentle wetting agent and shampoo and conditioner and softener components, all tested for low dermal irritation with a final pH below 4.5 and a viscosity of 1200 to 2000 CPS. The product reduces or eliminates the activity of live lice and makes it significantly easier to comb out nits. The product creates an environment repulsive to head lice thereby acting to prevent re-infestation. It is suited for the daily use that is necessary to insure permanent removal of all lice and nits by combing and serves to beautify the hair.

8 Claims, No Drawings

HOMEOPATHIC GENTLE SHAMPOO-CONDITIONER HEAD LICE REPELLENT AND NIT REMOVAL AID

FIELD OF THE INVENTION

This invention relates to the field of personal care products and more particularly to products for the treatment of head lice.

BACKGROUND OF THE INVENTION

Outbreaks of head lice, pediculus humanus Capitis, are near epidemic. In the United States it is estimated that ten to twelve million cases occur annually. This public health problem is considered by the uninformed to result from poor personal cleanliness. Thus the presence of head lice carries a social stigma. In actuality, poor personal cleanliness is not a major factor. Lice afflict individuals regardless of socio-economic status and in spite of adequate cleanliness. Infestation is endemic in populations of relatively high density where there is close physical contact and contact with articles used by others. Direct contact, as well as contact with combs, towels, bed linens, and/or clothing, are among things that can transfer the bugs. Unfortunately such contact is frequent in schools, particularly those with the very young; in summer camps; in military quarters and the like. These are characterized by high population density.

The approaches to treatment are insecticidal combined with manual removal, ovicidal with manual removal and simple manual removal.

Many insecticidal and ovicidal products have been used in the past. Some, once popular, have been removed from use because of extremely serious side effects especially when used on the young. Lindane is one example. Malathion is used but is extremely dangerous. There are natural products, folk remedies, that are of doubtful efficacy, which include mayonaise, vaseline, tea tree oil, and olive oil. These too have associated hazards often acting as growth sites for bacteria. There are natural products, remedies with insecticidal properties, that, being strong enough to kill lice, are seriously harmful to the skin of humans and can cause systemic disruptions. Many treatments are based on Pyrethrin and/or Permethrin. Again, the strengths needed can be harmful to the very young who are the most typical victims often through allergies. The FDA provides voluminous Adverse Effects reports listing serious side effects, including death, associated with use of pedulicides.

In addition, there is a large body of evidence indicating that the lice are becoming resistant to these chemicals as reported in PEDI Vol. 153 No. 9 pp 969–973 by Pollack et al. comparing treatment with permethrin of children suffering from pediculiasis in Massachusetts with similar children in Borneo. Most of the US children had previously been treated for lice. It was concluded that head lice in the United States are less susceptible to pyrethroids than those in Borneo where there is no history of prior exposure to the treatment. Similarly, a study in Israel ,Mumcuoglu et al., Medical and Veterinary Entomology (1995) 9. 427–432 concluded that lice were rapidly becoming resistant to permethrin; and in the Czech Republic, Rupes et al., Centr. Eur J. publ Hlth 3 no. 1. p. 330–32, found resistance to pyrethroids after exclusive use of lotions with cross-resistance to d-phenothrin and bioalethrin. Nevertheless, over-the-counter medications containing pediculicides and/or ovicides continue to be available for treatment of head lice.

In U.S. Pat. No. 4,518,593. Jouvin et al. teach an insecticide composition in the form of a shampoo that comprises 74–95% by volume of one of ammonium, triethanolamine, and sodium lauryl sulphate as a wetting agent, 2–12% by volume of acetic acid and 0.5–3% by volume of at least one of the group of natural or synthetic extracts or essences of clove, lavender, peppermint, organum, rosemary, lime, juniper, lemon, citronella, thyme, Datura Stramonium, pine, pyrethrum, pyrethrin and Ceylon cinnamon leaves, the pH of the composition being less than 4.5. The teaching is that the composition is effective in killing head lice. One of skill might well feel that the product is effective with such strong pediculocides as pyrethrin and that it should not be used on a frequent basis. This is especially so if the upper range of the acid is present. More important, insecticides, synthetic or natural, should not be in daily use for fear of harming the patient by absorption through the skin or at least harming the scalp and hair of the patient. As there is resistance to treatment on the part of typical users, the chance of overdose increases as parents, for example, use larger and more frequent doses than directed in order to obtain positive results.

Consider the pure manual approach. The National Pediculosis Association® (NPA), which can be contacted at http://www.headlice.org/, strongly urges manual removal to avoid the hazards associated with the strong chemicals, both natural and synthetic, required to kill lice. Their methodology involves the use of a fine-tooth comb (such as the LiceMeister® available from NPA) after careful de-tangling of the strands, augmented by tweezers, fingernails and p rhaps with double sided tape on a finger. Daily screening is recommended and frequent repetition of the procedure maybe required. One reason for this is because nits, the eggs, are extremely hard to remove and, if left, hatch new larvae. Another reason is that re-infestation often occurs because the victim continues to inhabit the environment where the infestation started. Moreover, manual removal is time-consuming and difficult. The lice and nits are firmly attached and hard to see. In addition, small children often object to combing with a fine tooth comb because the pulling action can be painful. This makes it unlikely that a consistent treatment course will be completed and can result in overlooked, live lice or, much more likely, nits that will insure re-infestation.

Therefor it is the object of this invention to provide a shampoo in combination with a hair conditioner that is gentle enough for daily use, beneficial to the hair, and does not contain harmful insecticides. It is an object to avoid toxicity and yet to be active in aiding manual removal of lice and nits by dislodging them. It is a further object to make fine combing painless for the victim so that a daily regimen can be followed with ease. Further, because many desirable ingredients mix poorly, it is an object of this invention to present a formula that meets the prime objectives and is stable. It is still a further object to provide a formulation that actively repels lice.

SUMMARY OF THE INVENTION

The invention is a homeopathic product for amelioration of infestation by head lice by providing a gentle, effective shampoo-conditioner for daily use that, when used with appropriate combing, acts as an aid to removing lice and nits, acts as an egg loosener and is a lice barrier. Th action of this formulation is nhanced by the incorporation of homeopathic insecticides to knockdown lice, the concentration of these homeopathic remedies being such that deleterious effects are avoided.

The objects of the invention are met by a formulation comprising a homeopathic insecticide added at a concentration in the range of 1x to 1c, with 15x preferred, wherein the homeopathic insecticide is selected from the group consisting of, lachesis, lycopodium, sulfur, vinca, natrum muriaticum, Apis Mellifica , Carbolicum Acidum, and Ledum Palustre to a core formula comprising an effective amount of acetic acid in association with a gentle wetting agent and shampoo and conditioner and softener components, all tested for low irritance, with a final pH below 4.5 and a viscosity of 1200 to 2000 CPS. Preferably the pH is in the range of about 3.0 to 3.5. The formula of the invention is nontoxic and stable. It is an excellent shampoo, conditioner and lubricating agent in the absence of the homeopathic ingredient but so constituted is not a deterrent. Without the homeopathic ingredient it helps in dislodging live lice and nits making removal up to 300 percent easier than a national brand over-the-counter remedy and the equal or superior of commercial anti-lice products. The at least one homeopathic insecticide is added at a concentration in the range of 1x to 1c, with about 15x preferred, to a core shampoo-conditioner formula wherein the homeopathic insecticide is selected from the group consisting of, lachesis, lycopodium, sulfur, vinca, Apis Mellifica, Carbolicum Acidum, Ledum Palustre, and natrum muriaticum and are added to the core formula to repel and further limit re-infestation without harm to the user. Surprisingly, the formulation of the invention inhibits the burrowing habit of head lice and significantly reduces the ability of female lice to attach nits to the hair.

The weight percent of the ingredients is: homeopathic element (the active ingredient) 1 to 10% with about 2.5% preferred; water, 40.8%; cocamidopropyl betaine, 40.0%; acetic acid, 5.0%; cationic 929, 4.0%; glycerin, 3%; ethylene glycol distearate, 1.7%: polyquaternium-10, 1.6%; Fragrance, 0.7%; diazolidum urea, 0.3%; methylparaben, 0.2%; propylparaben, 0.1%; tetrasodium EDTA, 0.1; FD&C Blue No.1, 0.5%; and FD&C Yellow No. 5. 0.5% and said ingredients are dispersed into intimate contact to form a stable gel emulsion at low pH less than 4.5 and a viscosity of 1200 to 2000 CPS, diazolidum urea; methylparaben; propylparaben; tetrasodium EDRA; FD&C Blue No.1; and FD&C Yellow No. 5 and said ingredients are dispersed into intimate contact to form a stable gel emulsion at low pH less than 4.5.

BRIEF DESCRIPTION OF THE DRAWINGS

FIGS. 1 through 5 are graphs depicting five successive days of repellency tests performed on the product of the invention.

DETAILED DESCRIPTION OF THE INVENTION

The invention is a homeopathic improvement on a gentle shampoo-conditioner comprising: homeopathic element (the active ingredient) 1 to 10% with about 2.5% preferred; water: acetic acid 5.0%; cationic 929. 4.0%; glycerin, 3%; ethylene glycol distearate. 1.7%: polyquaternium-10, 1.6%: fragrance, 0.7%; diazolidum urea, 0.3%; methylparaben, 0.2%; propylparaben, 0.1%; tetrasodium EDTA, 0.1; FD&C Blue No.1, 0.5%, and FD&C Yellow No. 5, 0.5% and said ingredients are dispersed into intimate contact to form a stable gel emulsion at low pH less than 4.5 and a viscosity of 1200 to 2000 CPS.

Table I following shows the ingredient list and includes suppliers and specifications:

TABLE I

| NAME | USE | TYPICAL SUPPLIER | SPEC |
| --- | --- | --- | --- |
| Deionized water | — | | USP XXIII |
| Cocamidopropyl Betaine | Surfactant | Henkel, Ambler, PA | |
| Acetic Acid | Active | Spectrum, New Brunswick, NJ | USP XXII |
| Cationic 929 | Conditioner Enhance Shine | Dow, Midland MI | |
| Glycerin | Hold Moisture | Aerchem, Bloomington, IN | USP XXII |
| Ethylene Glycol Distearate | Pearlize | Lipo, Paterson, NJ | |
| Polyuquaternium-10 | Conditioner | Amerchol Corp, Edison, NJ | |
| Fragrance | | Intl Flav & Frag New York, NY | |
| Diazolidium Urea | Anti-bacterial | ISP Technologies, Charlotte, NC | |
| Methyle Paraben | Anti-fungal | Allchem Industries, Gainesville,, FL | |
| Propyl Paraben | Anti-fungal | Allchem Industries | |
| Tetrasodium EDTA | Water Softener | Dow, Midland MI | |
| FD&C Blue No. 1 | Color | Pylam, Tempe, AZ | |
| FD&C Yellow No. 5 | Color | Pylam | |

All of the ingredients are well known to those of skill in the art and are obtainable from many vendors.

The formula without the homeopathic element (the core formula) provides every advantage listed above except repellency. When the homeopathic element is included, the formulation becomes repellent as well, exhibits the capacity to knockdown lice if not to kill them and not only repels head lice but enhances inhibition of their behavior in burrowing into hair to lay nits.

The method of use is simple: shampoo, massaging gently, and leave for a four to five minutes. Rinse with warm water. Repeat the shampoo and rinse. Comb out the nits and any remaining lice using an appropriate comb started as close to the scalp as possible. Then, rinse. The shampoo-conditioning action makes it easier to comb the hair. The live lice are stunned or killed and dislodged from the hair and the nits are loosened enough so that they are easily removed by fine combing. Within one week of daily use repellency is observed.

Some notes on the ingredients follow. They are added in the order listed above and blended to yield the desired stable product:

Distilled or deionized water is important because of the pH and to insure the absence of bacteria and salts that may interact with the other ingredients. It is most important that the water complies with microbiological tests according to USP.

The urea is a preservative used only in the low quantity so that there is no interaction with other ingredients.

All ingredients must be mixed into intimate contact but after the gel is finished, the use of the high sheer mixer is avoided to avoid breaking the gel structure.

Acetic acid (pyroligneous acid purified). This is a major ingredient. It is similar to the citric acid common to many shampoos to lower pH and, probably to counteract some of the other more basic ingredients. We believe that it aids in making an environment unfriendly to live lice especially in combination with the homeopathic ingredient as will be seen. As will be discussed below, tests have shown that live lice contacted by the product of this invention do not burrow through treated hair to get to the scalp unlike untreated hair where the burrowing is instantaneous and rapid. The acid is added very slowly during processing to avoid local stress in the gel caused by low pH.

Cocamidopropyl Betaine is the surfactant/detergent used. It is a product obtained from the fatty acids of natural coconut oil and exhibits very low dermic irritation. It works in low pH. Amphoteric characteristics of this surfactant make the formula of the invention compatible with either cationic or anionic ingredients which permits the mixing of all the components into a very stable composition under low pH.

Cationic 929 is the conditioner agent used. This contains an effective percentage of active surface agents and it is responsible for the hair-softener action of the formula. It works in low pH and is the major contributor allowing the user to comb the hair with a fine comb after shampooing and rinsing the hair.

Glycerine is a softener which works in conjunction with the conditioner. It also gives a marble appearance to the product.

The other ingredients provide the factors that consumers desire in personal care products:

Essence (fragrance) is added last to provide the desired odor. As is well known, the formulation of a particular essence usually is unknown the exact formulation being a trade secret of the vendor. Essences are known to be active with regard to other ingredients. An essence, therefore, must be tested with a formula to assure it will not affect its appearance or function during the useful life of the product.

Product specifications are:

| Aspect: | Liquid cream |
| --- | --- |
| Color | Light green |
| Odor: | Light vinegar |
| pH (100%) limits | ⁻3.00–⁻4.50 |
| Viscosity (100%) (Brookfield LVT, spindle T-A at 6 rpm, 25 degrees Celsius | 1200–1900 cps |
| Density (100%): | 0.980–1.100 g/ml |
| Assay: (Acetic acid: | 4.70–5.30 g % (w/v) |
| Microbiological Purity: | per USP XXIII, page 1680 |

Tests were carried out to evaluate the effectiveness first of the core formula, the ingredients of the invention without the homeopathic element, and then of the homeopathic formula.

EXAMPLE I

Tests of the non-homeopathic (core) formulation were conducted by a clinical laboratory (Hilltop Research Associates (HTR) of West Palm Beach, Fla.) to asses the utility of the formula in an uncontrolled study. Using four subjects who were lice infested the test protocol evaluated the efficacy of the shampoo/conditioner of this invention TEST I. Four female subjects between the ages of seven and fifteen, diagnosed with active pediculosis were enrolled in a study. Upon entering the study all four subjects were shampooed with the core product of this invention, waited two minutes, rinsed and shampooed again. The hair was combed with a nit comb to remove all live lice, both adult and nymph, and nits. Both the technician and the investigator observed that the experimental shampoo facilitated the ease of combing. Following combing, the subjects rinsed their hair and were evaluated. After these procedures the lice subjected to the shampoo/conditioner of the invention appeared stunned and remained in that condition for about twenty minutes. It was noted that the stunned lice were more readily removed from the hair by the use of continuous strong water pressure than untreated lice.

Aft r treatment, the subjects received a supply of the core formula and instructions for home daily use over a three week period. Two subjects were instructed to follow the procedure above. Two subjects were instructed to use the shampoo as above but not to use a nit comb. All subjects returned for evaluation at one, two and three weeks post treatment, Evaluations included the presence/absence of live lice and nits and an estimate of the number of lice and nits present. Subjects were also monitored by telephone contact and product usage weight was checked. Table II summarizes the results:

TABLE II

| | NO. LICE/NITS | | | |
| --- | --- | --- | --- | --- |
| SUBJECT | BASELINE | WEEK 1 | WEEK 2 | WEEK 3 |
| $001^1$ | 30/500 | None/None | None/30 | 3 nymphs/$40^3$ |
| $003^1$ | 20/250 | None/10 | None/None | None/none |
| $004^2$ | 30/300 | 1 nymph/40 | 4*/100++ | 1*/$100^4$ |
| $005^2$ | 20/400 | none/36 | 4*/100++ | 12*/$100^4$ |

*Adults
[1]Used nit comb with daily treatment
[2]Did not use nit comb with daily treatment
[3]Re-infestation from several household members infested but not on treatment
[4]May be re-infestation or hatching of nits This study indicates that the core shampoo-conditioner, when properly used as a daily shampoo with combing significantly aids in the removal of live lice and nits from the hair.

EXAMPLE II

Tests were conducted to compare the core formula with a leading shampoo Product X as control and a leading over-the-counter shampoo Product claiming to loosen eggs.

A bridge was provided between two subjects, one treated with the core formula and the other with Product X and lice were placed on the bridge one at a time and observed for ten minutes. Although the lice were not repelled by the core formula of the invention, their movement appeared to be slowed in that lice traveled on the outer perimeter of the hair and did not move into the scalp during the tem minutes of observation. The lice remained on the hair of the treated subject while the lice on the untreated subject immediately burrowed into the scalp suggesting a barrier action associated with the core formula. The final lice location was two on each subject and six on the bridge. The lice appeared to have no preference for migrating toward either treatment suggesting no repellency.

EXAMPLE III

The test was repeated with the two other subjects with similar results, Eleven lice were used and the final positions were two on each subject and the remainder on the bridge. The conclusion was as before that the lice appeared to have no preference for either treatment but the product of the invention acted as a barrier to activity of the lice that migrated on to the treated hair.

EXAMPLE IV

The hair of two subjects was placed on Petri dishes while the subject's heads rested on a table. Five lice were added to each dish. The observation was that overall neither product repelled the lice which appeared to move toward the respective scalps. The core product of the invention appeared to slow the movement of the lice and inhibit burrowing. The Product X shampoo did not inhibit the lice which burrowed actively.

EXAMPLE V

Test IV was repeated with the two other subjects with similar results.

EXAMPLES VI AND VII

Hairs were collected from children prior to treatment. Subjects were selected from a population having active cases of Pediculosis with at least 100 nits attached to their hair. Four subjects were tested. At least twenty-five hairs were cut from each subject with nits attached. The hairs were treated with the core product of the invention, with water or with a commercial nit loosener (Y) just prior to analysis. The grams of force required to displace the nits was measured using a modified tensile strength method previously used to test hair strength. Some hairs were not tested because they were too short. The difference between the mean force of removal value for the groups was evaluated using Student's t-test for independent data: that is treating each hair as independent from the others. Hypotheses testing was performed at the alpha=0.05 level. Table III shows the results.

TABLE III

FORCE REQUIRED TO REMOVE NITS (GRAMS)

| VALUE | TREATED | WATER | Y Nit Loosening Gel |
|---|---|---|---|
| Mean | 1.94 | 5.74 | 5.94 |
| Std Dev | 1.00 | 2.64 | 2.43 |

Anova p-value 0.0001

The data indicate about a three-fold reduction in force for the core formula of the invention compared to the brand-name control, a nit loosener, and to water.

Tests were then run by an independent biomedical investigator on the homeopathic formulation—the preferred product of the invention. Hair strands bearing fifty nits were rinsed in warm water for 30 seconds, exposed to the solution of the invention for 5 minutes, rinsed with warm water for 30 seconds, exposed to the solution of the invention for 5 minutes and rinsed with warm water for 30 seconds to simulate a procedure which would be followed by a consumer. A tensile test was then run to measure the force exerted in removing the nits. Table IV shows the results and a comparison with previously run tests (not from the same lice nor run at the same time) using 3 commercial products and 3 experimental products.

TABLE IV

| PRODUCT | MEAN FORCE (dynes) | STD DEV | MEDIAN |
|---|---|---|---|
| Invention | 2.900 | 1.452 | 2.747 |
| Product #1 | 3.400 | 1.600 | 3.100 |
| Product #2 | 3.100 | 2.100 | 3.000 |
| Product #3 | 2.000 | 0.800 | 1.600 |
| Exp. Prod #1 | 3.300 | 1.800 | 3.100 |
| Exp. Prod #2 | 2.000 | 1.500 | 1.800 |
| Exp. Prod #3 | 2.200 | 1.500 | 2.000 |

As an aid to easy combing, the product of the invention ranks with the better of the formulations tested.

We do not know the mechanism by which the product works. It is suspected that the glue of the nits is sufficiently reduced that the product can wick beneath and aid in removal as the comb is passed through the hair by lubricating the hair shaft. We believe that when force is applied to a nit through a comb the ingrdients are wicked in and the hair shaft is lubricated so that the nit slides off the hair. We believe that the product, while gentle to the hair and scalp, kills lice and/or renders them comatose loosening their grip and so making them easier to remove with rinsing and combing. Because lice and nit removal by manual means is the best and safest practice, the gentle nature of the product permits the needed daily treatment. It reduces the reluctance of the infested subject to submit to the treatment and, because of the conditioner component of the formula, aids in improving the softness and appearance of the hair despite the frequency of application. Thus, aid in combing, however it occurs, is important in a treatment regime.

Repellency per se was not established with the core formula in the test program. Re-infestation took place on some subjects as there was no control to ensure daily use at home by the subjects. Test data show that daily use with proper combing should prevent re-infestation but a formulation that did provide repellancy would provide even greater value in use. This advantage was found with the homeopathic formula of the invention.

An enhanced, lice-repellent, safe insecticidal action that does not alter the gentle character of the product clearly is indeed a desirable attribute to have for a shampoo/conditioner aimed at aiding removal by comb of lice and nits. We have found this can be done employing homeopathic principles. The core formula was modified by adding homeopathic insecticides in the range of 1x to 1c with 15x concentration preferred. These homeopathic insecticides include: Apis Mellifica, Carbolicum Acidum, Ledum Palustre, lachesis, lycopodium, sulfur , vinca and natrum muriaticum.

That the homeopathic product of the invention exhibited repellency was demonstrated in the following tests performed by an independent laboratory:

EXAMPLE VII

In the in vitro methodology used to simulate in vivo repellency, one half ounce human hair tresses were employed. A new white cheese cloth towel made of 100% cotton was machine washed in hot water containing a small amount of Product X original concentrate to soften the towel and remove any sizing or other residues. The towel was then thoroughly rinsed with clear hot water and dried in a clothes dryer. No fabric softeners, bleach or other laundry products were used. Disks about 245 mm×245 mm were cut from the prepared towel and stored in a clear Nalgene® screw cap jar to prevent contamination.

For each day of experiment, adult female and male head lice were collected from the heads of infested people. The lice were pooled in a petri dish containing a cloth disk dampened with filtered water. The lice were not identified as coming from any particular individual.

At the time of testing, the investigators placed a single cloth disk in a sterile petri dish measuring 245 mm×245 mm×25 mm. The repellent formula to be used was shaken several times and 19 ml was applied to a one half ounce ponytail tress. This was sufficient to saturate the tresses. The control tresses were washed in Product X, The petri dish was labeled with the product code number and application time (exposure) was recorded daily. All tests were conducted under artificial conditions of 74° F. and relative humidity of 72%.

Repellency was assessed on a daily basis over five days. Head lice repellency was determined by counting the number of lice on the control side and on the test formula side.

Day 1. Tresses, test and control, were shampooed twice at 5 minute intervals, air dried for 45 minutes, dried for 15 minutes with a portable drier, and placed on opposite sides of the petri dish. Nineteen adult lice were placed in the center. Behavior was observed at 5 minute intervals. The results are shown in FIG. 1. The product of the invention started repellency after 20 minutes of exposure when 63% of the lice had moved to the control side. After two hours, 79% had moved opposite the test side and remained there for the remaining two hours. It was observed that lice while on the side treated by the test product never burrowed into the hair nor did they lay any eggs. On the opposite (control) side, two nits were found Day 2. The tresses were not shampooed to see if repellency persisted. Ten healthy lice were removed from infested subjects and pooled for about a half hour in a dampened petri dish to prevent dehydration. The test and control tresses were placed on opposite side of a petri dish as before and the ten lice placed in the center. Results are seen in FIG. 2. After one hour the majority of the lice started to move closely toward the control side. After two hours eight lice (80%) were under the control tress and two lice were on top of the tress treated the day before with the product of the invention. These two did not burrow. Repellency after 4 hours was 80%. Then the lice wee removed. The tresses were shampooed as before and left to dry.

Day 3. The hair tresses which had been treated and allowed to dry for 13 hours were put under a dryer for ten minutes and placed on opposite side of the petri dish and seven adult lice were placed in the center of the dish. The results are shown in FIG. 3. The lice did not react for 55 minutes. Then the large majority of the lice moved toward the control side. After one hour 71% were on the control side and remained there, two remained on the test tress. After 4 hours the lice were discarded and the tresses shampooed twice at 5 minute intervals as before and left to dry.

Day 4. The tresses were dried and put in place. Five live lice were placed in the center. Within thirty minutes three were on the control side and two on the test side. See FIG. 4. Twenty minutes later the two went directly to the control side yielding 100% repellency after 40 minutes. The lice were discarded after four hours and the tresses were shampooed as before and left to dry.

Day 5. Placement was made as before and five lice placed in the center. See results in FIG. 5. Within one hour zero percent were on the test side and 100% on the control side and remained there for the rest of the test.

The scientists carrying out the tests made these observations: the time for repellency varied with the average being one hour: lice found on the tresses treated with the product of the invention surprisingly never burrowed into the hair and always remained on the surface of the tress, a behavior noted as unusual females laid eggs on the control side but not on the test side; and damp hair has greater repellency. It was suggested by the scientists that since the lice did not explore the test product treated hair, it was unlikely that they would survive on the human host head of hair.

What is claimed is:

1. A gentle shampoo-conditioner for daily use that aids in combing out lice and nits from the hair comprising a stable emulsion gel having active ingredients of:
   i) cocoamidopropyl betaine;
   ii) acetic acid
   iii) cationic 929
   iv) glycerin
   v) ethylene glycol distearate
   vi) polyquaternium-10 and
   vii) inactive ingredients; and further comprising an effective amount of at least one homeopathic insecticide at a concentration in the range of 1x to 1c; wherein said emulsion has a pH of less than 4.5 and the homeopathic insecticide is selected from the group consisting of lachesis, lycopodium, sulfur, vinca natrum muriaticum, Apis Mellifica, Carbolicom Acidum, and Ledum Palustre.

2. The shampoo-conditioner of claim 1 wherein said emulsion has a viscosity of 1200 to 2000 cps.

3. The shampoo-conditioner of claim 2 wherein the pH is in the range of about 3.0 to 3.5.

4. The shampoo-conditioner of claim 1 wherein the weight percent of the active ingredients are:
   Cocoamidopropyl 40%; acetic acid 5.0%; Cationic 929, 4%; glycerin 3.0%; Ethylene Glycol Distearate 1.7%; Polyquaternium-10 1.6%; and said ingredients are dispersed into intimate contact with the balance of said inactive ingredients and with said homeopathic insecticide.

5. The shampoo conditioner of claim 4 wherein said inactive ingredients that are dispersed into intimate contact comprise:

| | |
|---|---|
| i) Distilled or deionized water | 40.8%; |
| ii) Diazolidinyl Urea | 0.3% |
| iii) methylparaben | 0.2% |
| iv) Propylparaben | 0.1% |
| v) Tetrasodium EDTA | 0.1% and |
| vi) Fragrance and Color | 1.7%; | whereby said stable emulsion gel can be formed at said pH.

6. The shampoo-conditioner of claim 3 wherein the homeopathic insecticide is selected from the group consisting of Apis Mellifica, Carbolicom Acidum, and Ledum Palustre.

7. The shampoo-conditioner of claim 3 wherein the homeopathic ingredient is about 15x.

8. The shampoo-conditioner of claim 3 wherein the weight percent of the homeopathic ingredient is about 2.5.

* * * * *